(12) United States Patent
Suzuki

(10) Patent No.: US 11,980,359 B2
(45) Date of Patent: May 14, 2024

(54) BI-DIRECTIONAL MEDICAL SUTURING DEVICE

(71) Applicant: KANEKA CORPORATION, Osaka (JP)

(72) Inventor: Shohei Suzuki, Settsu (JP)

(73) Assignee: KANEKA CORPORATION, Osaka (JP)

( * ) Notice: Subject to any disclaimer, the term of this patent is extended or adjusted under 35 U.S.C. 154(b) by 724 days.

(21) Appl. No.: 17/274,904

(22) PCT Filed: Aug. 27, 2019

(86) PCT No.: PCT/JP2019/033432
§ 371 (c)(1),
(2) Date: Mar. 10, 2021

(87) PCT Pub. No.: WO2020/071012
PCT Pub. Date: Apr. 9, 2020

(65) Prior Publication Data
US 2022/0054124 A1   Feb. 24, 2022

(30) Foreign Application Priority Data
Oct. 1, 2018   (JP) .................................. 2018-186971

(51) Int. Cl.
*A61B 17/04* (2006.01)

(52) U.S. Cl.
CPC ...... *A61B 17/0469* (2013.01); *A61B 17/0491* (2013.01); *A61B 2017/047* (2013.01)

(58) Field of Classification Search
CPC ............ A61B 17/0469; A61B 17/0491; A61B 2017/047; A61B 2017/06042; A61B 2017/0472
See application file for complete search history.

(56) References Cited

U.S. PATENT DOCUMENTS 7,004,951 B2* 2/2006 Gibbens, III ...... A61B 17/0482
606/144
10,433,832 B2* 10/2019 Hasan ................ A61B 17/0485
(Continued)

FOREIGN PATENT DOCUMENTS

JP    2003-159254 A    6/2003
JP    2011-509121 A    3/2011
(Continued)

OTHER PUBLICATIONS

International Search Report (PCT/ISA/210) issued in PCT/JP2019/033432, dated Nov. 5, 2019.

*Primary Examiner* — Shaun L David
*Assistant Examiner* — Rachael L Geiger
(74) *Attorney, Agent, or Firm* — Birch, Stewart, Kolasch & Birch, LLP

(57) ABSTRACT

A bi-directional medical suturing device includes a first needle; a second needle being disposed distal to the first needle; a first thread control member including a first holding portion being movable between a position where the first holding portion prevents a movement of the first needle and a position where the first holding portion does not prevent the movement of the first needle; and a second thread control member including a second holding portion being located the first holding portion, the second holding portion being movable between a position where the second holding portion prevents a movement of the second needle and a position where the second holding portion does not prevent the movement of the second needle.

14 Claims, 6 Drawing Sheets

(56) References Cited

U.S. PATENT DOCUMENTS

| | | |
|---|---|---|
| 10,779,814 B2* | 9/2020 | Kurd ................. A61B 17/0469 |
| 2003/0139752 A1 | 7/2003 | Pasricha et al. |
| 2009/0177031 A1 | 7/2009 | Surti et al. |
| 2011/0028998 A1 | 2/2011 | Adams et al. |
| 2011/0082477 A1 | 4/2011 | Smith |
| 2011/0112555 A1 | 5/2011 | Overes et al. |
| 2013/0046319 A1 | 2/2013 | Arnett et al. |
| 2014/0058415 A1 | 2/2014 | Smith |
| 2014/0180313 A1 | 6/2014 | Harrison et al. |
| 2016/0249907 A1 | 9/2016 | Harrison et al. |
| 2016/0287247 A1 | 10/2016 | Smith |
| 2017/0150966 A1* | 6/2017 | Chin ................. A61B 17/0469 |
| 2018/0228487 A1 | 8/2018 | Smith |
| 2019/0365379 A1 | 12/2019 | Harrison et al. |

FOREIGN PATENT DOCUMENTS

| | | |
|---|---|---|
| JP | 2011-72790 A | 4/2011 |
| JP | 2012-515636 A | 7/2012 |
| JP | 2012-525224 A | 10/2012 |
| JP | 2014-528768 A | 10/2014 |
| WO | WO 2009/089101 A2 | 7/2009 |
| WO | WO 2010/085793 A2 | 7/2010 |
| WO | WO 2013/024466 A2 | 2/2013 |

* cited by examiner

[Fig. 1]
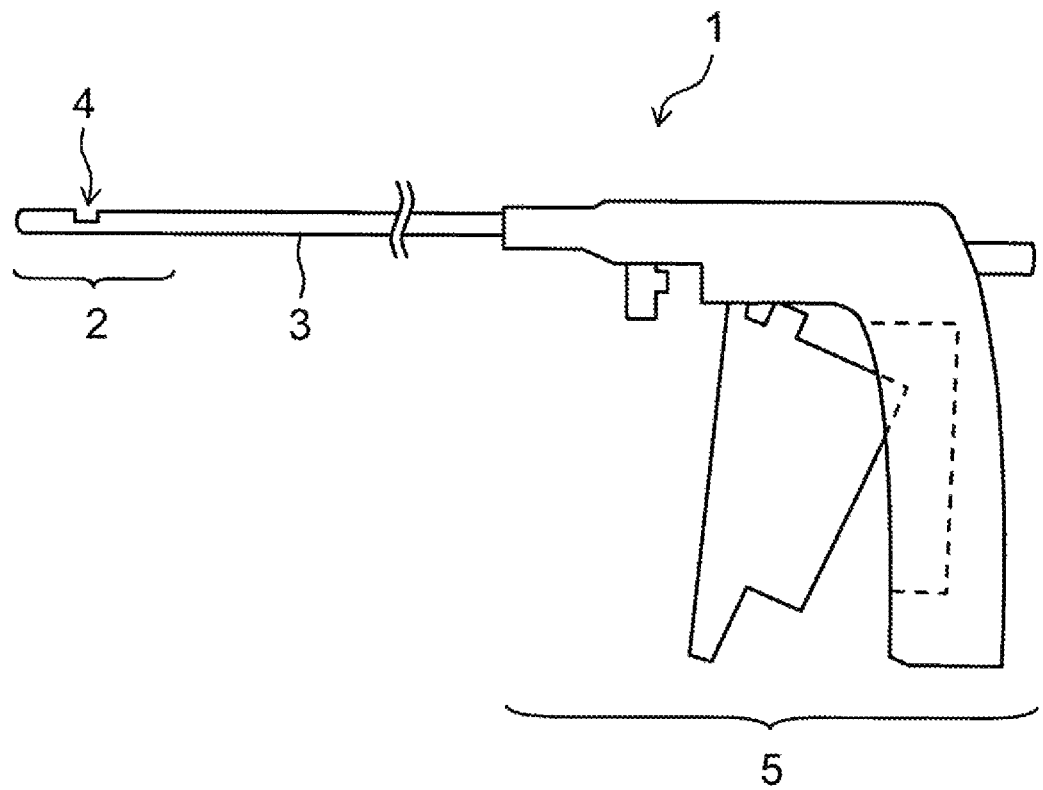
[Fig. 2]
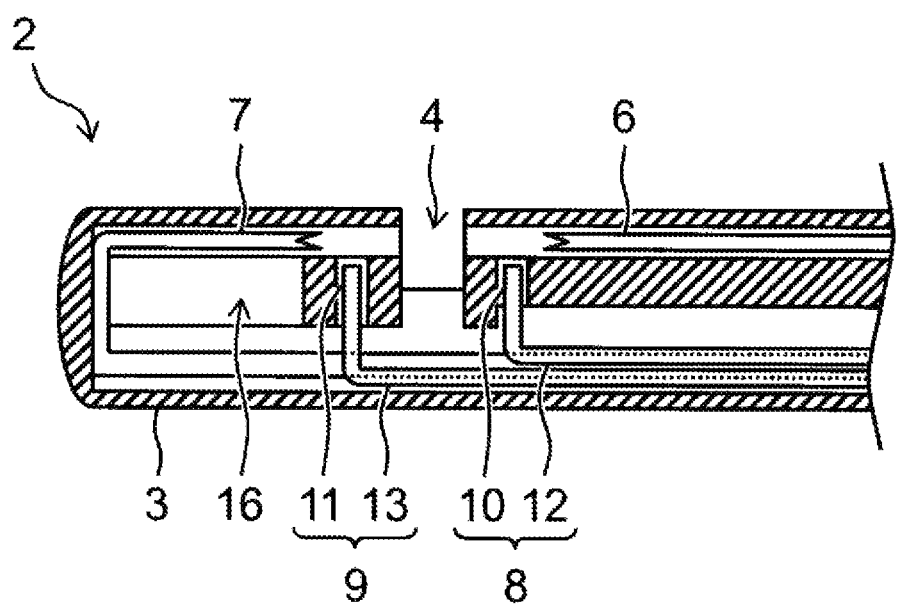

[Fig. 3]
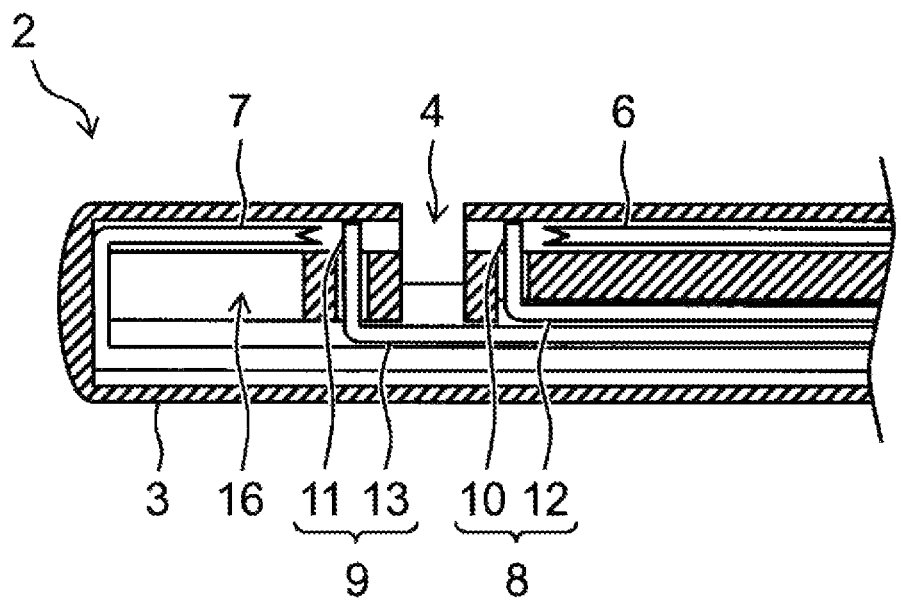
[Fig. 4]
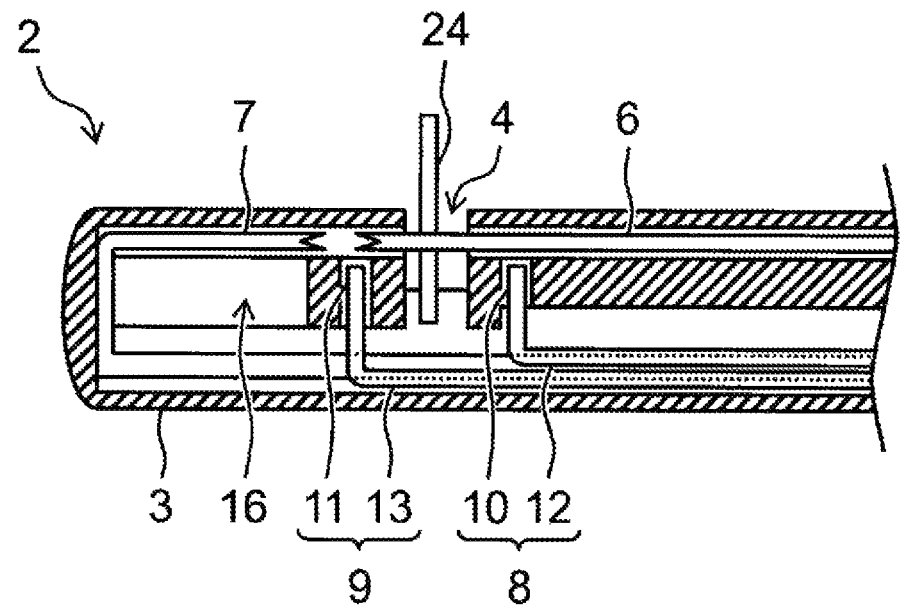

[Fig. 5]
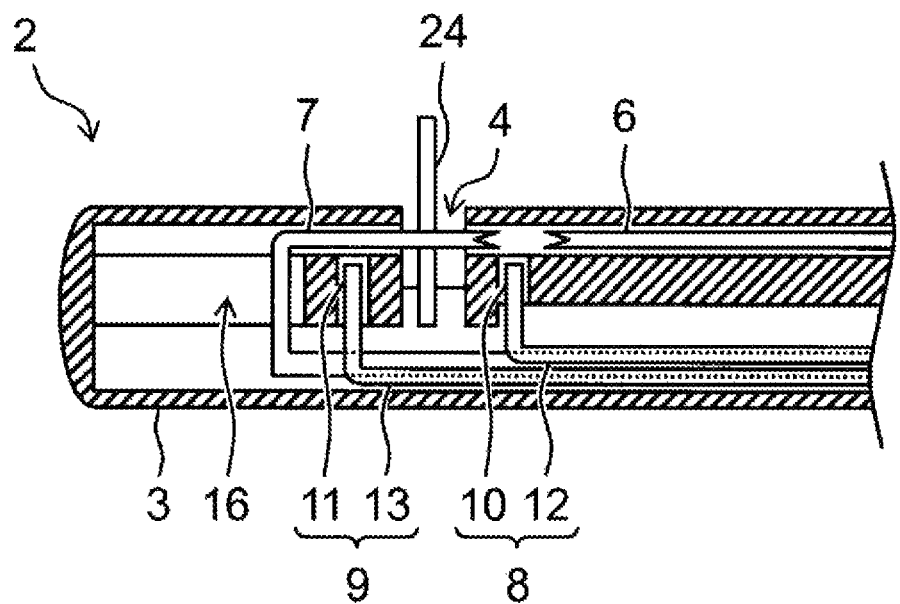
[Fig. 6]
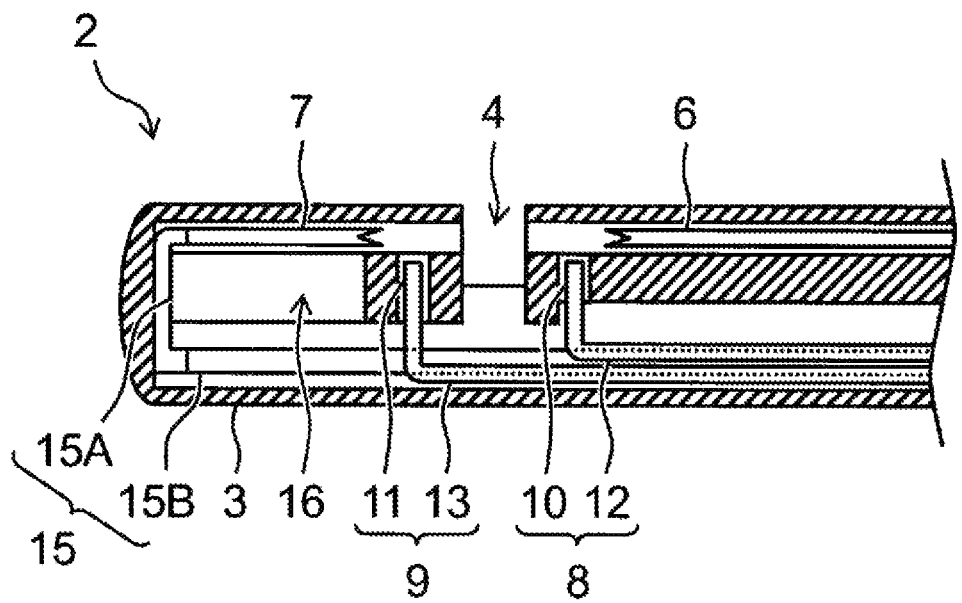

[Fig. 7]
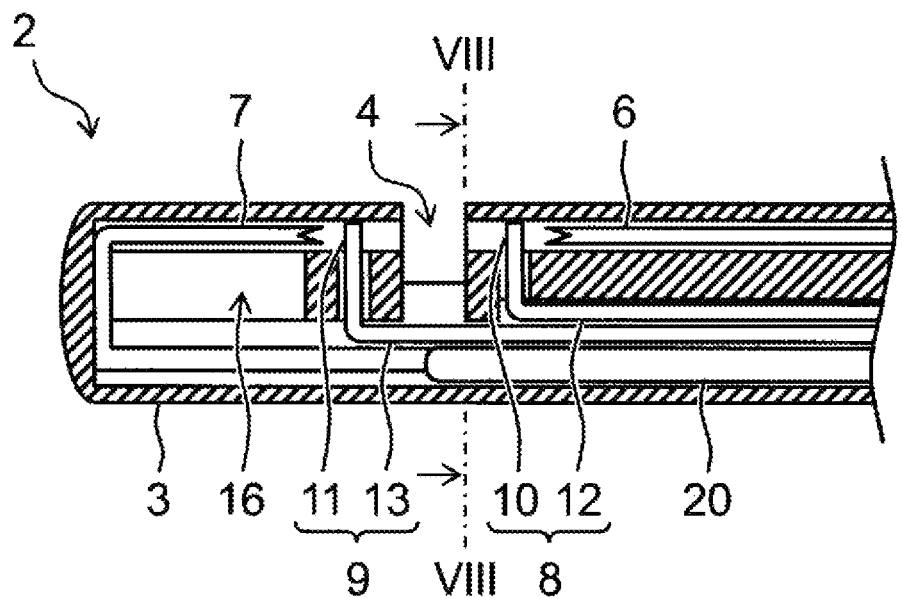
[Fig. 8]
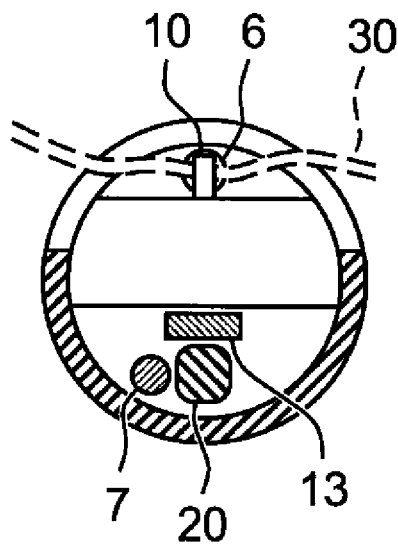

[Fig. 9]
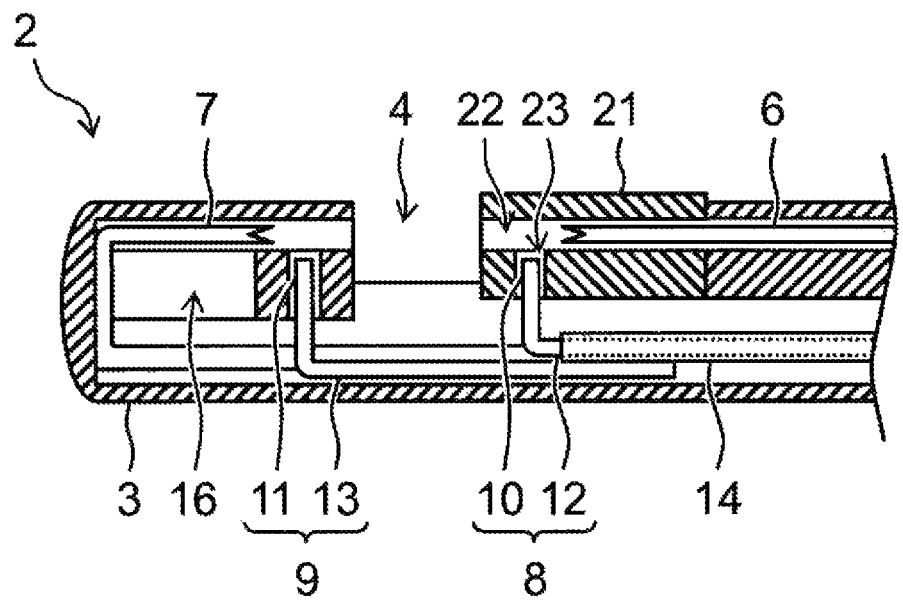
[Fig. 10]
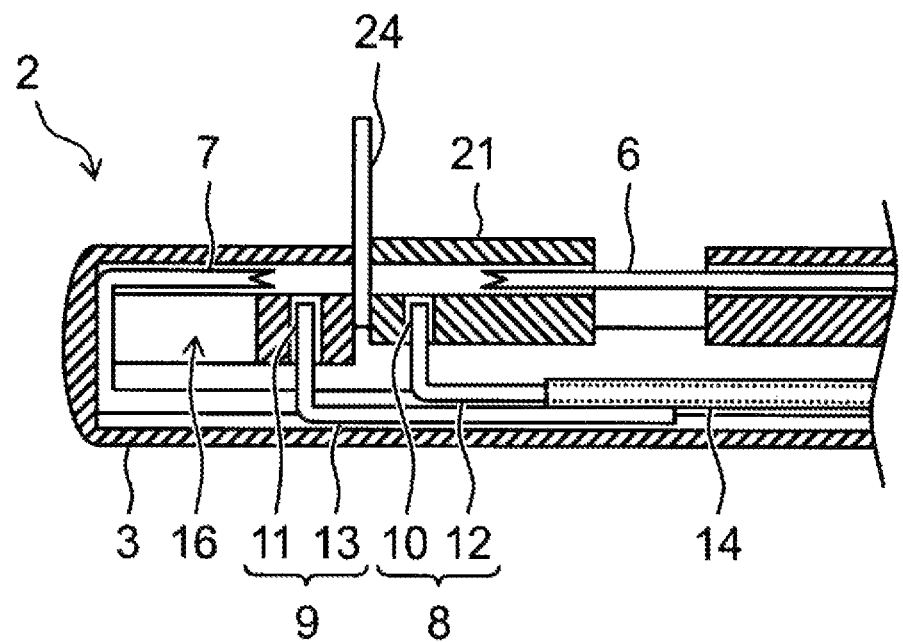

[Fig. 11]
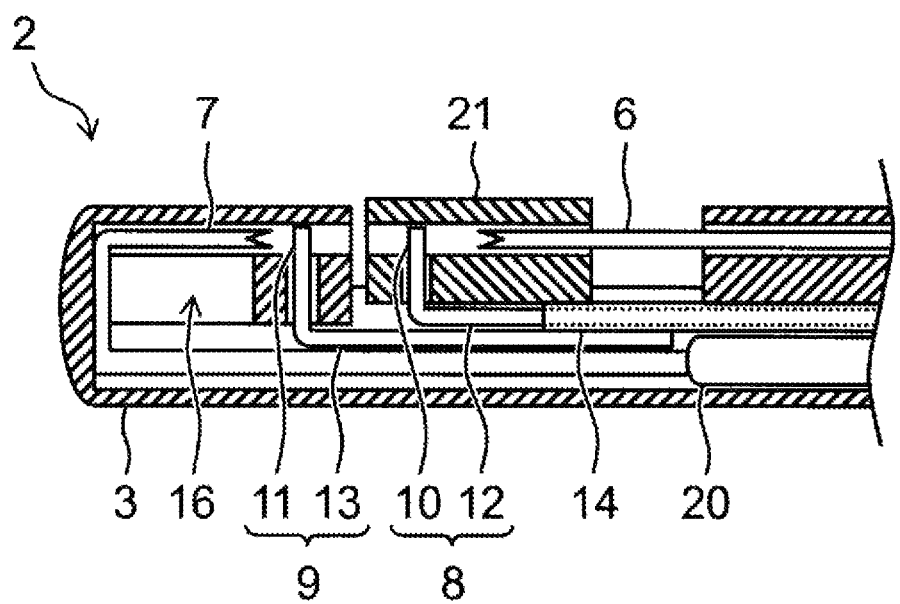

BI-DIRECTIONAL MEDICAL SUTURING DEVICE

TECHNICAL FIELD

The present invention relates to a bi-directional medical suturing device capable of suturing an object bi-directionally with a thread from a proximal side to a distal side and from the distal side to the proximal side.

BACKGROUND ART

Trans-sphenoidal surgery (TSS) is often performed to remove a tumor in the pituitary gland. TSS is generally performed by the following procedure. First, a surgeon advances along the patient's nasal septum while avulsing the nasal mucosa, fenestrates the sphenoid bone and opens the dura mater to reach the pituitary gland. The pituitary tumor is then removed and finally the dura mater is sutured to reconstruct the sphenoid bone and nasal mucosa. As a device for suturing the dura mater, a suturing device for bi-directionally passing a suture thread from a distal side to a proximal side and from the proximal side to the distal side of the dura mater has been proposed (for example, Patent Documents 1 to 7).

RELATED ART DOCUMENTS

Patent Documents

Patent Document 1: JP-T-2012-515636
Patent Document 2: WO 2010/085793
Patent Document 3: JP-T-2014-528768
Patent Document 4: WO 2013/024466
Patent Document 5: JP-A-2011-072790
Patent Document 6: JP-T-2011-509121
Patent Document 7: WO 2009/089101

SUMMARY OF THE INVENTION

Technical Problem

It is desirable that the medical suturing device is configured so that suture work of a membranal tissue and the like may be reliably performed while preventing the suture thread from falling out of the device by an easy operation. For example, threading devices disclosed in Patent Documents 1 and 2 have a problem that it is physically difficult to move a suture thread from a cutout of a needle into a groove of a distal boom arm housing. In devices disclosed in Patent Documents 3 to 5, it is necessary to make a knot on a suture thread and tie the same to a ferrule, so that these operations require time. In suture thread holders disclosed in Patent Documents 6 and 7, it is necessary to re-grip a needle and change a gripping position each time the needle is bi-directionally reciprocated.

The present invention has been made in view of the above circumstances, and an object thereof is to provide a bi-directional medical suturing device capable of easily performing suture work of a membranal tissue and the like while preventing a suture thread from falling out of the device.

Solutions to the Problems

The gist of a bi-directional medical suturing device according to the present invention that can overcome the above problems is as follows. A bi-directional medical suturing device includes a first needle having a tip directed toward a distal side, the first needle being distally and proximally movable; a second needle being disposed distal to the first needle, the second needle having a tip directed toward a proximal side, the second needle being distally and proximally movable; a first thread control member including a first holding portion being movable in a direction different from a distal direction toward a distal end of the device and being movable in a direction different from a proximal direction toward a proximal end of the device, the first holding portion being movable between a position where the first holding portion prevents a movement of the first needle and a position where the first holding portion does not prevent the movement of the first needle; and a second thread control member including a second holding portion being movable in a direction different from the distal direction and the proximal direction, the second holding portion being movable between a position where the second holding portion prevents a movement of the second needle and a position where the second holding portion does not prevent the movement of the second needle, the first holding portion being located distal to the first needle and proximal to the second needle and the second holding portion being located distal to the first holding portion and proximal to the second needle in a state where the first needle is located at the most proximal position and the second needle is located at the most distal position.

According to the bi-directional medical suturing device of the present invention, bi-directional suturing may be easily performed by using the first needle and the second needle. Since the first needle and the second needle act to transfer a thread forward by distal and proximal movement, a suturing mechanism may be configured relatively simply. Furthermore, by using the first thread control member and the second thread control member, it is possible to prevent the thread from falling out of the device at the time of suturing and to bi-directionally suture more reliably.

Preferably, the first holding portion is movable between the position where the first holding portion prevents a movement of the first needle and the position where the first holding portion does not prevent the movement of the first needle, and is movable between the position where the second holding portion prevents a movement of the second needle and the position where the second holding portion does not prevent the movement of the second needle, and/or the second holding portion is movable between the position where the second holding portion prevents a movement of the second needle and the position where the second holding portion does not prevent the movement of the second needle, and is movable between the position where the first holding portion prevents a movement of the first needle and the position where the first holding portion does not prevent the movement of the first needle.

Preferably, the first holding portion is movable in a direction perpendicular to a direction from a distal end to a proximal end of the device, and/or the second holding portion is movable in a direction perpendicular to a direction from a distal end to a proximal end of the device. In this case, preferably, the first holding portion has a rod shape extending in the direction perpendicular to the direction from the distal end to the proximal end of the device, and is movable in the direction perpendicular to the direction from the distal end to the proximal end of the device, and/or the second holding portion has a rod shape extending in the direction perpendicular to the direction from the distal end to the proximal end of the device, and is movable in the direction perpendicular to the direction from the distal end to the proximal end of the device.

Preferably, the first holding portion and the second holding portion are movable in the direction perpendicular to the direction from the distal end to the proximal end of the device and in the same direction as each other. Further, the first needle and the second needle are preferably overlapped with each other as seen from the distal side or the proximal side.

Preferably, the first thread control member preferably includes a first supporting portion extending in a direction from a distal end to a proximal end of the device, the first supporting portion being disposed proximal to the first holding portion, and/or the second thread control member includes a second supporting portion extending in the direction from the distal end to the proximal end of the device, the second supporting portion being disposed proximal to the second holding portion. In this case, the first thread control member and/or the second thread control member is preferably distally and proximally movable. Further, preferably, the first supporting portion includes a first tubular portion at least a part of which in the direction from the distal end to the proximal end of the device has a tubular shape, and the second supporting portion of the second thread control member is slidably disposed in the first tubular portion, or the second supporting portion includes a second tubular portion at least a part of which in the direction from the distal end to the proximal end of the device has a tubular shape, and the first supporting portion of the first thread control member is slidably disposed in the second tubular portion.

The bi-directional medical suturing device preferably further includes a membranal tissue fixing member distally and proximally movable. In this case, the fixing member preferably includes a first insertion passage extending in a direction from a distal end to a proximal end of the device in which the first needle and/or the second needle are insertable. Further, the fixing member preferably includes a second insertion passage extending in a direction different from the direction from the distal end to the proximal end of the device, and the first holding portion or the second holding portion is insertable into the second insertion passage. In this case, the first thread control member or the second thread control member may distally and proximally move by distally and proximally moving the fixing member.

Preferably, the first holding portion and the first supporting portion of the first thread control member are movable in the direction perpendicular to the direction from the distal end to the proximal end of the device, and the second holding portion and the second supporting portion of the second thread control member are movable in the direction perpendicular to the direction from the distal end to the proximal end of the device. In this case, when the direction perpendicular to the direction from the distal end to the proximal end of the device is set to an up-and-down direction, a direction in which the first holding portion moves from the position where the first holding portion prevents a movement of the first needle to the position where the first holding portion does not prevent the movement of the first needle is set to a downward direction, and a direction opposite to the downward direction is set to an upward direction, a spacer distally and proximally movable may be disposed under the first supporting portion and/or the second supporting portion, Further, it is possible configure such that the first holding portion and the first supporting portion move in the upward direction, and/or the second holding portion and the second supporting portion move in the upward direction by moving the spacer distally, and the first holding portion and the first supporting portion move in the downward direction, and/or the second holding portion and the second supporting portion move in the downward direction by moving the spacer proximally.

Advantageous Effects of the Invention

According to the bi-directional medical suturing device of the present invention, the first needle is used when transferring the thread from a proximal side to a distal side, and the second needle is used when transferring the thread from the distal side to the proximal side, so that a suture object such as a membranal tissue may be easily bi-directionally sutured. At that time, by using the first thread control member and the second thread control member, it is possible to prevent the thread from falling out of the device at the time of suturing and to suture more reliably.

BRIEF DESCRIPTION OF THE DRAWINGS

FIG. 1 is an example of a side view of a bi-directional medical suturing device.

FIG. 2 is an example of a cross-sectional view of a treatment portion on a distal side of the bi-directional medical suturing device, and a configuration example of the treatment portion in a state where a first holding portion of a first thread control member and a second holding portion of a second thread control member are in positions where they do not prevent movements of a first needle and a second needle.

FIG. 3 is an example of a cross-sectional view of the treatment portion on the distal side of the bi-directional medical suturing device, and a configuration example of the treatment portion in a state where the first holding portion of the first thread control member and the second holding portion of the second thread control member are in positions where they prevent the movements of the first needle and the second needle.

FIG. 4 is an example of a cross-sectional view of the treatment portion on the distal side of the bi-directional medical suturing device, and a configuration example of the treatment portion in a state where a suture object is punctured with the first needle.

FIG. 5 is an example of a cross-sectional view of the treatment portion on the distal side of the bi-directional medical suturing device, and a configuration example of the treatment portion in a state where a suture object is punctured with the second needle.

FIG. 6 is an example of a cross-sectional view of the treatment portion on the distal side of the bi-directional medical suturing device, and a configuration example in which the second needle is attached to a handle via a connector.

FIG. 7 is an example of a cross-sectional view of the treatment portion on the distal side of the bi-directional medical suturing device, and a configuration example of the treatment portion in which a spacer is provided under the first thread control member and the second thread control member.

FIG. 8 is a cross-sectional view taken along VIII-VIII of FIG. 7

FIG. 9 is an example of a cross-sectional view of the treatment portion on the distal side of the bi-directional medical suturing device, and a configuration example of the treatment portion in which a membranal tissue fixing member is provided.

FIG. 10 is an example of a cross-sectional view of the treatment portion on the distal side of the bi-directional medical suturing device, and a configuration example of the treatment portion in which a membranal tissue fixing member is provided.

FIG. 11 is an example of a cross-sectional view of the treatment portion on the distal side of the bi-directional medical suturing device, and a configuration example of the treatment portion in which a membranal tissue fixing member is provided, and the spacer is provided under the first thread control member and the second thread control member.

DESCRIPTION OF EMBODIMENTS

The present invention relates to a bi-directional medical suturing device capable of bi-directionally passing a thread through a suture object such as a membranal tissue from a first side to a second side and from the second side to the first side. The bi-directional medical suturing device of the present invention includes a first needle that transfers the thread from a proximal side to a distal side, a second needle that transfers the thread from the distal side to the proximal side, and a first thread control member and a second thread control member for preventing the thread transferred by each needle from falling out of the device. According to the bi-directional medical suturing device of the present invention, bi-directional suturing may be easily performed by using the first needle and the second needle. Since the first needle and the second needle act to transfer the thread forward by distal and proximal movement, a suturing mechanism may be configured relatively simply. Furthermore, by using the first thread control member and the second thread control member, it is possible to prevent the thread from falling out of the device at the time of suturing and to bi-directionally suture reliably.

The bi-directional medical suturing device of the present invention will be specifically explained below based on the following embodiments, however, the present invention is not restricted by the embodiments described below of course, and can be certainly put into practice after appropriate modifications within in a range meeting the gist of the above and the below, all of which are included in the technical scope of the present invention. In the drawings, hatching, a reference sign for a member may be omitted for convenience, and in such a case, the description and other drawings should be referred to. In addition, sizes of various members in the drawings may differ from the actual sizes thereof, since priority is given to understanding the features of the present invention.

FIG. 1 illustrates a side view of an entire bi-directional medical suturing device, and FIGS. 2 to 5 illustrate an example of a cross-sectional view of a treatment portion on a distal side of the bi-directional medical suturing device. Meanwhile, in this specification, the "bi-directional medical suturing device" is sometimes simply referred to as a "suturing device".

A suturing device 1 includes a treatment portion 2 for suturing a suture object such as a membranal tissue on a distal side, and a handle 5 for operating the treatment portion 2 on a proximal side. The treatment portion 2 includes a first needle 6, a second needle 7, a first thread control member 8, and a second thread control member 9, and it is possible to suture the membranal tissue and the like by operating these members. The handle 5 is provided with a lever, a button and the like for operating each member of the treatment portion 2.

In the present invention, the proximal side of the suturing device refers to a side in a direction toward a user's hand, and the distal side refers to a side in a direction opposite to the proximal side, that is, the direction toward a treated object. In FIGS. 1 to 5, a left side of the drawing is the distal side, and a right side of the drawing is the proximal side. A direction from one of the proximal side and the distal side to the other of the suturing device is referred to as a distal direction toward a distal end of the device or a proximal direction toward a proximal end of the device.

A size of the suturing device 1 in a direction from a distal end to a proximal end of the device may be set with a distance from the user's hand to the suture object as a guide, and may be set to, for example, 5 cm or more and 80 cm or less. In trans-sphenoidal surgery (TSS), this may be set with reference to a distance from the pituitary gland to the nostril, and is preferably 20 cm or more and 50 cm or less, for example.

Each portion of the suturing device 1 is preferably made of a biocompatible material. Examples of such material include a metal material such as stainless steel and a resin material, for example. Especially, a portion inserted into a body is preferably made of a biocompatible material or provided with a biocompatible coating layer.

The first needle 6 having a tip directed toward the distal side is distally and proximally movable. The second needle 7 disposed distal to the first needle 6 and having a tip directed toward the proximal side is distally and proximally movable. As illustrated in FIG. 4, by disposing a membranal tissue 24 being the suture object between the tip of the first needle 6 and the tip of the second needle 7, and threading the first needle 6 and distally moving the same, it is possible to pass the thread through the suture object from the proximal side to the distal side. As illustrated in FIG. 5, by threading the second needle 7 and proximally moving the same, it is possible to pass the thread through the suture object from the distal side to the proximal side. At that time, the thread transferred by the first needle 6 from the proximal side through the suture object to the distal side moves from a first needle 6 side to a second needle 7 side. The thread transferred by the second needle 7 from the distal side through the suture object to the proximal side moves from the second needle 7 side to the first needle 6 side. As a result, it becomes possible to distally and proximally move the thread and suture the suture object. It is possible to suture, for example, by passing the thread from the proximal side to the distal side by the first needle 6 through a portion on a first side and passing the thread from the distal side to the proximal side by the second needle 7 through a portion on a second side across an incision line of the membranal tissue and the like.

The suturing device 1 includes a main body portion disposed distal to the handle 5. The main body portion includes a tubular body 3 extending in the direction from the distal end to the proximal end of the device, and the first needle 6 and the second needle 7 are preferably disposed in the tubular body 3. The tubular body 3 is preferably provided with a cutout 4 in which the suture object is disposed. It is only required that the cutout 4 be provided in at least a part between the tip of the first needle 6 and the tip of the second needle 7 of the tubular body 3. In detail, it is only required that the cutout 4 be provided in at least a part of a portion distal to the tip of the first needle 6 and proximal to the tip of the second needle 7 of the tubular body 3 in a state where the first needle 6 is located at the most proximal position and the second needle 7 is located at the most distal position. The cutout 4 may also be formed so as to extend proximally to the tip of the first needle 6 and/or distally to the tip of the second needle 7.

The tubular body 3 is preferably provided with an insertion passage through which the first needle 6 passes and/or an insertion passage through which the second needle 7 passes. By providing these insertion passages, trajectories of movements of the first needle 6 and the second needle 7 are stabilized. Therefore, a first holding portion 10 of the first thread control member 8 described later may be easily correctly moved to a position where this prevents the movement of the first needle 6, and a second holding portion 11 of the second thread control member 9 may be easily correctly moved to a position where this prevents the movement of the second needle 7.

The first needle 6 is preferably movable to a position proximal to the tip of the second needle 7 and preferably does not reach a position distal to the tip of the second needle 7 in a state where the second needle 7 is located at the most distal position. The second needle 7 is preferably movable to a position distal to the tip of the first needle 6 and preferably does not reach a position proximal to the tip of the first needle 6 in a state where the first needle 6 is located at the most proximal position. As a result, when the first needle 6 or the second needle 7 is threaded and distally and proximally moved, it is possible to preferably deliver the thread between the proximal side and the distal side of the suture object, in other words, between the first needle 6 side and the second needle 7 side.

The first needle 6 and the second needle 7 are preferably overlapped with each other as seen from the distal side or the proximal side, and it is more preferable that an axial center of the first needle 6 and an axial center of the second needle 7 coincide with each other. The fact that the first needle 6 and the second needle 7 overlap with each other as seen from the distal side or the proximal side means that the first needle 6 and the second needle 7 are substantially collinear in the direction from the distal end to the proximal end of the device. In this case, at least the tip of the first needle 6 and the tip of the second needle 7 are preferably overlapped with each other as seen from the distal side or the proximal side. By disposing the first needle 6 and the second needle 7 in this manner, the thread distally moved by the first needle 6 may be easily disposed near the tip of the second needle 7, and the thread proximally moved by the second needle 7 may be easily disposed near the tip of the first needle 6. Therefore, it becomes possible to preferably deliver the thread between the first needle 6 side and the second needle 7 side. In a case where it is difficult to puncture the suture object with the threaded needle out of the first needle 6 and the second needle 7, it becomes possible to facilitate the suturing of the suture object by opening a hole on the suture object with the unthreaded needle.

The thread is not especially limited as long as it is a suture thread used for medical purposes, and may be a single thread or a knitting thread. A diameter of the thread may be appropriately selected as long as it is a diameter generally used for the suture thread. A material of the thread may be a degradable material. A length of the thread is desirably sufficiently long so as not to interfere with the surgery, and preferably 20 cm or more and 200 cm or less. For example, in TSS, a length obtained by adding a sufficient length for a surgeon to make a knot of the suture thread outside a patient's body to a length for allowing the suture thread to reciprocate between the outside the body and the dura mater is preferred, and a preferable length of the thread in TSS is 40 cm or more and 150 cm or less.

The first and second needles 6 and 7 are preferably made of a biocompatible material strong enough for puncturing the suture object such as a body tissue. The first and second needles 6 and 7 are preferably made of, for example, a metal material such as stainless steel or a resin material, and more preferably made of stainless steel from the viewpoint of safety and ease of processing.

The first and second needles 6 and 7 may be solid or hollow. Meanwhile, from the viewpoint of ease of manufacturing and high strength, the first and second needles 6 and 7 are preferably solid.

Outer diameters of the first and second needles 6 and 7 are not especially limited as long as they are diameters used in general suture needles, but are preferably 0.05 mm or more and 1.5 mm or less, for example. In a case where the first and second needles 6 and 7 are hollow, wall thicknesses are preferably 0.01 mm or more and 0.5 mm or less, for example.

Lengths of the first and second needles 6 and 7 may be appropriately set in a range of 1.5 mm or more and 40 cm or less being a distance from the nasal cavity to the pituitary gland, for example, for use in TSS.

The first needle 6 and the second needle 7 may be directly connected to the handle 5, or may be connected to the handle 5 via one or a plurality of connectors. By connecting the first needle 6 and the second needle 7 directly or indirectly to the handle 5, it is possible to operate the handle 5 on a hand side to distally and proximally move the first needle 6 and the second needle 7.

A tip end of each of the first and second needles 6 and 7 is preferably formed so that a cross-sectional area becomes smaller toward the tip, and as a result, the suture object is easily punctured with the first and second needles 6 and 7.

It is preferable that the tip of each of the first and second needles 6 and 7 is at least split into a first end and a second end. Each of the first and second needles 6 and 7 may have three or more ends at the tip. As a result, when the first needle 6 is moved distally or the second needle 7 is moved proximally, it is possible to hook the thread on the split portion of the first needle 6 or the second needle 7. The split portion of each needle preferably has a groove shape at a predetermined angle with respect to an advancing direction of the needle, that is, in the direction from the distal end to the proximal end of the device, and is disposed perpendicular to the direction from the distal end to the proximal end of the device, for example. When the thread is hooked on such a split portion, the thread may be moved along with the distal and proximal movement of the first needle 6 and the second needle 7, and the thread may be easily passed through the suture object. Meanwhile, a peak of each of the first and second needles 6 and 7 is preferably located, at the peak, on an outer periphery of a portion on a base side of the end of the needle or in an inner portion of a range around the outer periphery. This makes it easier to pass the needle through the suture object. It is also preferable that each tip end of the split end is formed so as to be tapered toward the tip. Tip positions of the split ends may be the same as or different from each other in the direction from the distal end to the proximal end of the device. The number of splits at each of the tips of the first and second needles 6 and 7 is not especially limited as long as it is two or more, but eight or less is preferable, six or less is more preferable, and four or less is further preferable. Especially, as illustrated in the drawing, it is preferable that the tip of each of the first and second needles 6 and 7 is split into two.

An entire shape of each of the first and second needles 6 and 7 may be a straight line, a curved line, or a combination thereof. The first and second needles 6 and 7 may have a bent part. In FIG. 2, the second needle 7 is provided with the bent part. With the bent part in the second needle 7, the tip of the second needle 7 is formed to face the proximal side and a base end side of the second needle 7 is also formed to face the proximal side, so that the second needle 7 may be connected to the handle 5. In order to allow a connecting portion connecting a portion extending in the direction from the distal end to the proximal end of the device of the tip side of the second needle 7 and a portion extending in the direction from the distal end to the proximal end of the device of the base end side thereof to be distally and proximally movable, a passage 16 through which the connecting portion passes is formed distal to the cutout 4 in the tubular body 3.

It is also possible that the second needle 7 is not provided with the bent part, and a connector extending in the direction from the distal end to the proximal end of the device is provided on a distal end of the second needle 7, and the second needle 7 is connected to the handle 5 via this connector. FIG. 6 illustrates an example in which the second needle 7 is connected to the handle 5 via a connector 15. As illustrated in FIG. 6, the second needle 7 may be connected to the handle 5 via one or a plurality of connectors 15. It is also possible that the second needle 7 is not provided with the bent part, and the second needle 7 is connected to the handle 5 via a first connector 15A extending in a direction perpendicular to the direction from the distal end to the proximal end of the device and a second connector 15B extending in the direction from the distal end to the proximal end of the device. In a case of connecting the second needle 7 to the handle 5 via the connector 15, the second needle 7 may have the bent part and the number of connectors 15 may be one or two or more without being limited to the example of FIG. 6.

Although not illustrated in the drawing, a protective lid covering the cutout 4 may be attached to the tubular body 3. As a result, when the tubular body 3 is moved in the body before and after the suturing, the tips of the first needle 6 and the second needle 7 may be prevented from being exposed from the cutout 4. The protective lid is preferably attached so as to be distally and proximally movable, for example. It is also preferable that the protective lid may be opened and closed with the handle 5 on the hand side. As a result, the protective lid may be moved to expose the cutout 4 at the time of suturing, and the cutout 4 may be covered with the protective lid at the time of non-suturing.

The suturing device 1 is provided with the first thread control member 8 and the second thread control member 9 so as to prevent the thread from falling out of the device when the first needle 6 transfers the thread from the proximal side of the suture object or the second needle 7 transfers the thread from the distal side of the suture object. The first thread control member 8 is provided so as to regulate the movement of the thread transferred by the first needle 6, and the second thread control member 9 is provided so as to regulate the movement of the thread transferred by the second needle 7. The second thread control member 9 is provided so that at least a part thereof is located distal to the first thread control member 8. The first thread control member 8 and the second thread control member 9 are preferably disposed in the tubular body 3.

The first thread control member 8 includes the first holding portion 10 movable in a direction different from the distal direction and the proximal direction, and movable between a position where this prevents the movement of the first needle 6 and a position where this does not prevent the movement of the first needle 6. The second thread control member 9 includes the second holding portion 11 movable in a direction different from the distal direction and the proximal direction, and movable between a position where this prevents the movement of the second needle 7 and a position where this does not prevent the movement of the second needle 7. Then, the first holding portion 10 is located distal to the tip of the first needle 6 and proximal to the tip of the second needle 7 and the second holding portion 11 is located distal to the first holding portion 10 and proximal to the tip of the second needle 7 in a state where the first needle 6 is located at the most proximal position and the second needle 7 is located at the most distal position. When suturing with the suturing device, it is preferable that the suture object is disposed between the first holding portion 10 and the second holding portion 11, and therefore, the first holding portion 10 is preferably disposed proximal to a position where the suture object is disposed in the suturing device and the second holding portion 11 is preferably disposed distal to the position. In the drawing, the first thread control member 8 and the second thread control member 9 are formed into an L shape in a cross-section in the direction from the distal end to the proximal end of the device, and tip ends of portions extending perpendicularly to the direction from the distal end to the proximal end of the device being distal portions serve the first holding portion 10 and the second holding portion 11, respectively.

By moving in a direction different from the distal direction and the proximal direction, the first holding portion 10 may move between the position where this prevents the movement of the first needle 6 and the position where this does not prevent the movement of the first needle 6. By moving in a direction different from the distal direction and the proximal direction, the second holding portion 11 may move between the position where this prevents the movement of the second needle 7 and the position where this does not prevent the movement of the second needle 7. FIG. 2 illustrates a state where the first holding portion 10 and the second holding portion 11 are in the positions where they do not prevent the movements of the first needle 6 and the second needle 7, respectively, and FIG. 3 illustrates a state where the first holding portion 10 and the second holding portion 11 are in the positions where they prevent the movements of the first needle 6 and the second needle 7, respectively. FIGS. 2 to 5 illustrate, as an example in which the first holding portion 10 and the second holding portion 11 move in a direction different from the distal direction and the proximal direction, an aspect in which they move in the direction perpendicular to the direction from the distal end to the proximal end of the device.

When the first holding portion 10 moves to the position where this prevents the movement of the first needle 6, it is possible to prevent the thread to be transferred by the first needle 6 from easily falling out of the device. On the other hand, in a case where the first holding portion 10 is in the position where this does not prevent the movement of the first needle 6, it is possible to transfer the thread by distally moving the first needle 6. When the second holding portion 11 moves to the position where this prevents the movement of the second needle 7, it is possible to prevent the thread to be transferred by the second needle 7 from easily falling out of the device. On the other hand, in a case where the second holding portion 11 is in the position where this does not prevent the movement of the second needle 7, it is possible to transfer the thread by proximally moving the second needle 7.

The first holding portion 10 and the second holding portion 11 may prevent the thread from falling out by directly coming into contact with the thread, or may prevent the thread from falling out by moving to the positions where they interfere with the thread when the thread falls out.

The position where the movement of the first needle 6 is prevented is on the trajectory of the first needle 6 when the first needle 6 is distally and proximally moved, and an arbitrary position distal to the tip of the first needle 6 in a state where the first needle 6 is located at the most proximal position. The position where the movement of the second needle 7 is prevented is on the trajectory of the second needle 7 when the second needle 7 is distally and proximally moved, and an arbitrary position proximal to the tip of the second needle 7 in a state where the second needle 7 is located at the most distal position.

The moving directions of the first holding portion 10 and the second holding portion 11 are not especially limited as long as they are directions different from the distal direction and the proximal direction. It is preferable that the first holding portion 10 and the second holding portion 11 are translated in a direction different from the distal direction and the proximal direction by operation of the handle 5. The direction different from the distal direction and the proximal direction is preferably a direction of 45° or more and 90° or less, more preferably a direction of 60° or more and 90° or less, and further preferably a direction of 75° or more and 90° or less with respect to the direction from the distal end to the proximal end of the device from the viewpoint of effectively preventing the thread from falling out. The first holding portion 10 and/or the second holding portion 11 are/is preferably movable especially in the direction perpendicular to the direction from the distal end to the proximal end of the device, and as a result, when the first holding portion 10 or the second holding portion 11 is moved, the thread is less likely to shift in the distal direction and the proximal direction even when the first holding portion 10 or the second holding portion 11 comes into contact with the thread.

The moving directions of the first holding portion 10 and the second holding portion 11 may be the same as or different from each other. Even in a case where the first holding portion 10 and the second holding portion 11 are movable in the directions perpendicular to the direction from the distal end to the proximal end of the device, the moving directions of the first holding portion 10 and the second holding portion 11 may be the same as or different from each other. Meanwhile, from the viewpoint of making the treatment portion 2 compact, it is preferable that the first holding portion 10 and the second holding portion 11 are movable in the same direction as each other.

It is especially preferable that the first holding portion 10 and the second holding portion 11 are formed to be movable in the direction perpendicular to the direction from the distal end to the proximal end of the device and in the same direction as each other. In this case, the direction perpendicular to the direction from the distal end to the proximal end of the device may be an up-and-down direction. A direction in which the first holding portion 10 moves from the position where this prevents the movement of the first needle 6 to the position where this does not prevent the movement of the first needle 6, or a direction in which the second holding portion 11 moves from the position where this prevents the movement of the second needle 7 to the position where this does not prevent the movement of the second needle 7 may be set to a downward direction, and a direction opposite to this may be set to an upward direction.

The first holding portion 10 is preferably movable between the position where this prevents the movement of the first needle 6 and the position where this does not prevent the movement of the first needle 6, and preferably movable between the position where this prevents the movement of the second needle 7 and the position where this does not prevent the movement of the second needle 7. The second holding portion 11 is preferably movable between a position where this prevents the movement of the second needle 7 and the position where this does not prevent the movement of the second needle 7, and preferably movable between the position where this prevents the movement of the first needle 6 and the position where this does not prevent the movement of the first needle 6. With the first holding portion 10 and the second holding portion 11 provided in this manner, it is possible to prevent the thread from falling out of the suturing device while the thread transferred from the proximal side through the suture object to the distal side by the first needle 6 moves to the second needle 7 or while the thread transferred from the distal side through the suture object to the proximal side by the second needle 7 moves to the first needle 6.

The shapes of the first holding portion 10 and the second holding portion 11 are not especially limited. Meanwhile, from the viewpoint of making a space in which the first holding portion 10 and the second holding portion 11 move in the tubular body 3 as small as possible, and making it easier to prevent the thread from falling out by the movements of the first holding portion 10 and the second holding portion 11, the first holding portion 10 preferably has a rod shape or a plate shape extending in a direction different from the distal direction and the proximal direction and is movable in this direction, and the second holding portion 11 preferably has a rod shape or a plate shape extending in a direction different from the distal direction and the proximal direction and is movable in this direction. From the viewpoint of saving the space in the tubular body 3 of the first holding portion 10 and the second holding portion 11, each of the first holding portion 10 and the second holding portion 11 more preferably has the rod shape extending in the direction different from the distal direction and the proximal direction. As described above, since the first holding portion 10 and/or the second holding portion 11 are/is preferably movable in the direction perpendicular to the direction from the distal end to the proximal end of the device, the first holding portion 10 preferably has the rod shape or the plate shape extending in the direction perpendicular to the direction from the distal end to the proximal end of the device and is movable in the direction, and the second holding portion 11 preferably has the rod shape or the plate shape extending in the direction perpendicular to the direction from the distal end to the proximal end of the device and is movable in the direction. Furthermore, each of the first holding portion 10 and the second holding portion 11 more preferably has the rod shape extending in the direction perpendicular to the direction from the distal end to the proximal end of the device.

It is preferable that the tubular body 3 is provided with an insertion passage through which the first holding portion 10 passes and/or an insertion passage through which the second holding portion 11 passes. The insertion passage through which the first holding portion 10 passes preferably extends in the moving direction of the first holding portion 10, that is, a direction different from the distal direction and the proximal direction, and preferably extends in the direction perpendicular to the direction from the distal end to the proximal end of the device. The insertion passage through which the second holding portion 11 passes preferably extends in the moving direction of the second holding portion 11, that is, a direction different from the distal direction and the proximal direction, and preferably extends in the direction perpendicular to the direction from the distal end to the proximal end of the device. By providing these insertion passages, it becomes easier to move the first holding portion 10 and the second holding portion 11 in a desired direction different from the distal direction and the proximal direction, and correctly move them to the position where they prevent the movement of the first needle 6 or the position where they prevent the movement of the second needle 7. The insertion passage through which the first holding portion 10 passes is preferably connected to the middle of the insertion passage through which the first needle 6 passes, and the insertion passage through which the second holding portion 11 passes is preferably connected to the middle of the insertion passage through which the second needle 7 passes. It is preferable that the cutout 4 of the tubular body 3 is provided distally to the insertion passage through which the first holding portion 10 passes and proximally to the insertion passage through which the second holding portion 11 passes.

The first thread control member 8 and the second thread control member 9 are preferably made of a biocompatible material. The first and second thread control members 8 and 9 are preferably made of, for example, a metal material such as stainless steel or a resin material, and more preferably made of stainless steel from the viewpoint of safety and ease of processing.

The first holding portion 10 of the first thread control member 8 and the second holding portion 11 of the second thread control member 9 preferably move between the position where they prevent the movement of the first needle 6 or the second needle 7 and the position where they do not prevent the movement of the first needle 6 or the second needle 7 by operation of the handle 5 on the hand side. From this viewpoint, the first thread control member 8 preferably includes a first supporting portion 12 extending in the direction from the distal end to the proximal end of the device disposed proximal to the first holding portion 10, and the second thread control member 9 preferably includes a second supporting portion 13 extending in the direction from the distal end to the proximal end of the device disposed proximal to the second holding portion 11. In this case, by operating the first supporting portion 12 extending more proximally than the first holding portion 10, the first holding portion 10 may be moved in a predetermined direction different from the distal direction and the proximal direction, and by operating the second supporting portion 13 extending more proximally than the second holding portion 11, the second holding portion 11 may be moved in a predetermined direction different from the distal direction and the proximal direction.

The first holding portion 10 and the first supporting portion 12 of the first thread control member 8 may be integrally formed of one member, or may be formed by combining a plurality of members. The second holding portion 11 and the second supporting portion 13 of the second thread control member 9 may be integrally formed of one member, or may be formed by combining a plurality of members. In either case, a positional relationship of the first holding portion 10 with respect to the first supporting portion 12 and a positional relationship of the second holding portion 11 with respect to the second supporting portion 13 are fixed, and an angle between the first holding portion 10 and the first supporting portion 12 and an angle between the second holding portion 11 and the second supporting portion 13 are preferably fixed regardless of the operation of the first thread control member 8 and the second thread control member 9. In FIGS. 2 to 5, a tip end on the distal side obtained by bending a wire rod into an L shape is made the first or second holding portion 10 or 11, and a portion proximal to the same is made the first or second supporting portion 12 or 13.

The first thread control member 8 preferably includes the first holding portion 10 and the first supporting portion 12 movable in the direction perpendicular to the direction from the distal end to the proximal end of the device, and the second thread control member 9 preferably includes the second holding portion 11 and the second supporting portion 13 movable in the direction perpendicular to the direction from the distal end to the proximal end of the device. When the first holding portion 10 and the first supporting portion 12 may be integrally moved in the direction perpendicular to the direction from the distal end to the proximal end of the device, and the second holding portion 11 and the second supporting portion 13 may be integrally moved in the direction perpendicular to the direction from the distal end to the proximal end of the device in this manner, the first holding portion 10 and the second holding portion 11 may be stably moved in the direction perpendicular to the direction from the distal end to the proximal end of the device.

It is preferable that the first thread control member 8 and the second thread control member 9 are movable in the direction perpendicular to the direction from the distal end to the proximal end of the device and in the same direction as each other. In this case, the first supporting portion 12 of the first thread control member 8 and the second supporting portion 13 of the second thread control member 9 may be disposed adjacent to each other in the direction perpendicular to the direction from the distal end to the proximal end of the device, so that a space required for the movement of the first thread control member 8 and the second thread control member 9 in the tubular body 3 may be made further smaller.

It is preferable that the first thread control member 8 and the second thread control member 9 are formed to be movable in the direction perpendicular to the direction from the distal end to the proximal end of the device in the following manner. That is, it is preferable that, when the direction perpendicular to the direction from the distal end to the proximal end of the device in which the first holding portion 10 is movable is set to the up-and-down direction, the direction in which the first holding portion 10 moves from the position where this prevents the movement of the first needle 6 to the position where this does not prevent the movement of the first needle 6 is set to the downward direction, and the direction opposite to this is set to the upward direction, a spacer distally and proximally movable is disposed under the first supporting portion 12 and/or the second supporting portion 13, by moving the spacer distally, the first holding portion 10 and the first supporting portion 12 move in the upward direction, and/or the second holding portion 11 and the second supporting portion 13 move in the upward direction, and by moving the spacer proximally, the first holding portion 10 and the first supporting portion 12 move in the downward direction, and/or the second holding portion 11 and the second supporting portion 13 move in the downward direction. More preferably, both the first holding portion 10 and the second holding portion 11 move in the up-and-down direction due to the distal and proximal movement of the spacer.

FIGS. 7 and 8 illustrate a configuration example in which a spacer 20 distally and proximally movable is provided under the first supporting portion 12 and the second supporting portion 13. FIG. 7 illustrates a cross-sectional view of the treatment portion 2 in the direction from the distal end to the proximal end of the device, and FIG. 8 illustrates a cross-sectional view taken along VIII-VIII of the treatment portion 2 of FIG. 7, that is, a cross-sectional view perpendicular to the direction from the distal end to the proximal end of the device in which a state where the first holding portion 10 is disposed in the position where this prevents the movement of the first needle 6 is illustrated. In FIG. 8, a suture thread 30 is indicated by a dashed-dotted line. As illustrated in FIG. 7, when the spacer 20 is distally moved, the first holding portion 10 and the first supporting portion 12 move in the upward direction, and the second holding portion 11 and the second supporting portion 13 move in the upward direction. On the other hand, the state illustrated in FIG. 2 may be regarded as a state where the spacer 20 is proximally moved. When the spacer 20 is proximally moved, the first holding portion 10 and the first supporting portion 12 move in the downward direction, and the second holding portion 11 and the second supporting portion 13 move in the downward direction.

A position in the direction from the distal end to the proximal end of the device of the spacer 20 may be appropriately adjusted so that the first holding portion 10 and/or the second holding portion 11 may move in the up-and-down direction when the spacer 20 is distally and proximally moved. For example, if the first holding portion 10 and the second holding portion 11 move in the upward direction to the positions where they prevent the movements of the first needle 6 and/or the second needle 7 when a distal end of the spacer 20 is located proximal to the first holding portion 10 and the second holding portion 11, it is not necessarily required to move the spacer 20 to the position under the first holding portion 10 and the second holding portion 11, that is, the position in the direction from the distal end to the proximal end of the device of the first holding portion 10 and the second holding portion 11 when the spacer 20 is distally moved.

As the spacer 20, it is preferable to use a rod-shaped or plate-shaped member extending in the direction from the distal end to the proximal end of the device. By using such a spacer 20, the spacer 20 may be disposed and distally and proximally moved even in a narrow space in the tubular body 3.

In a case of providing the spacer 20 under the first supporting portion 12 and/or the second supporting portion 13, a force in the downward direction preferably acts on the first thread control member 8 and the second thread control member 9 when the spacer 20 is proximally moved. As a result, when the spacer 20 is proximally moved, the first thread control member 8 and the second thread control member 9 are easily move in the downward direction. Therefore, it is preferable that the first supporting portion 12 and/or the second supporting portion 13 are/is in contact with an elastic member such as a spring or rubber. For example, it is possible to allow the downward force to act on the first supporting portion 12 and/or the second supporting portion 13 by providing a compression coil spring, a torsion spring, or a leaf spring above the first supporting portion 12 and/or the second supporting portion 13, by providing an extension coil spring under the first supporting portion 12 and/or the second supporting portion 13, or by connecting the first supporting portion 12 and/or the second supporting portion 13 to the tubular body 3 under the same with rubber, elastic string, or elastic thread. As yet another example, it is possible to allow the downward force to act on the first supporting portion 12 and/or the second supporting portion 13 by providing rubber, an elastic string, or an elastic thread so as to enclose the first supporting portion 12 and/or the second supporting portion 13 and orbit a cross-section as seen in the direction from the distal end to the proximal end of the device of the tubular body 3 of a portion including the cutout 4. As a result, when the spacer 20 is proximally moved, the first thread control member 8 and/or the second thread control member 9 are/is easily move in the downward direction.

Although not illustrated in the drawing, a protrusion may be provided on an inner surface of the tubular body 3 located under the first supporting portion 12 and/or the second supporting portion 13. In this case, it is preferable that a part of the first supporting portion 12 and/or a part of the second supporting portion 13 and the tip end of the spacer 20 are fixed to each other. When the spacer 20 is distally moved, the tip end of the spacer 20 abuts the protrusion and rides thereon, so that the first thread control member 8 and/or the second thread control member 9 may be moved in the upward direction. When the spacer 20 is proximally moved, the tip end of the spacer 20 descends from the protrusion, so that the first thread control member 8 and/or the second thread control member 9 may be moved in the downward direction.

A method of moving the first holding portion 10 and the second holding portion 11 in the up-and-down direction is not limited to the method described above. For example, by providing a space in which a distal portion of the first thread control member 8 and a distal portion of the second thread control member 9 may move in the up-and-down direction under the first thread control member 8 and the second thread control member 9 and connecting a wire to the distal portion of the first thread control member 8 and the distal portion of the second thread control member 9 to pull the wire proximally, the first holding portion 10 and the second holding portion 11 may be formed to be movable in the up-and-down direction. It is also possible that each of the first holding portion 10 and the second holding portion 11 has a magnetic material, and by distally moving the spacer having a magnetic material to approach to the first holding portion 10 and the second holding portion 11, the first holding portion 10 and the second holding portion 11 are moved in the upward direction by a repulsive force of the magnetic material, and by proximally moving the spacer to separate from the first holding portion 10 and the second holding portion 11, the first holding portion 10 and the second holding portion 11 are moved in the downward direction. In this case, it is possible that the first thread control member 8 only includes the first holding portion 10, and the second thread control member 9 only includes the second holding portion 11.

It is preferable that the first thread control member 8 and/or the second thread control member 9 may also distally and proximally move. In this case, it is preferable to distally and proximally move the first thread control member 8 in the extending direction of the first supporting portion 12, and to distally and proximally move the second thread control member 9 in the extending direction of the second supporting portion 13. By distally and proximally moving the first thread control member 8 or the second thread control member 9, the position in the direction from the distal end to the proximal end of the device in which the first holding portion 10 or the second holding portion 11 regulates the thread may be adjusted.

In a case where the first thread control member 8 and/or the second thread control member 9 are/is formed to be distally and proximally movable, the first thread control member 8 and the second thread control member 9 are preferably formed as illustrated in FIG. 9, for example. That is, it is preferable that the second supporting portion 13 includes a second tubular portion 14 at least a part of which in the direction from the distal end to the proximal end of the device is in a tubular shape, and that the first supporting portion 12 of the first thread control member 8 is slidably disposed in the second tubular portion 14. In FIG. 9, the second tubular portion 14 is provided side by side to a proximal portion of the wire rod formed into an L shape of the second supporting portion 13 in the direction perpendicular to the direction from the distal end to the proximal end of the device, and the second tubular portion 14 is joined to the L-shaped wire rod. The second tubular portion 14 is provided as a part of the second supporting portion 13. When the first supporting portion 12 of the first thread control member 8 and the second supporting portion 13 of the second thread control member 9 are formed in this manner, the first supporting portion 12 slides in the second tubular portion 14, so that the space required for the distal and proximal movement of the first thread control member 8 and the second thread control member 9 in the tubular body 3 becomes smaller. The distal and proximal movement of the first thread control member 8 or the second thread control member 9 may be stabilized. Meanwhile, although not illustrated in the drawing, it is possible that the first supporting portion 12 includes a first tubular portion at least a part of which in the direction from the distal end to the proximal end of the device is in a tubular shape, and that the second supporting portion 13 of the second thread control member 9 is slidably disposed in the first tubular portion.

As illustrated in FIGS. 9 and 10, the suturing device preferably includes a membranal tissue fixing member 21 for fixing the membranal tissue to be sutured. The membranal tissue fixing member 21 is formed to be distally and proximally movable, and by distally and proximally moving the same, it is possible to clamp and fix the membranal tissue 24 to be sutured. As a result, puncture with the first needle 6 and the second needle 7 becomes easy. Hereinafter, the "membranal tissue fixing member" is sometimes simply referred to as a "fixing member".

It is preferable that the fixing member 21 is disposed in the tubular body 3 and is disposed in the cutout 4 of the tubular body 3 described above. FIG. 9 illustrates the suturing device in a state before clamping the membranal tissue, and FIG. 10 illustrates a configuration example of the suturing device in a state where the membranal tissue 24 is clamped. FIGS. 9 and 10 illustrate a configuration example of the suturing device capable of clamping the membranal tissue when the fixing member 21 is distally moved, and in this case, a distal end of the fixing member 21 is preferably located distal to the tip of the first needle 6 and proximal to the tip of the second needle 7 in a state where the first needle 6 is located at the most proximal position and the second needle 7 is located at the most distal position. Although not illustrated in the drawing, the fixing member 21 may clamp the membranal tissue when proximally moved, and in this case, a proximal end of the fixing member 21 is preferably located distal to the tip of the first needle 6 and proximal to the tip of the second needle 7 in a state where the first needle 6 is located at the most proximal position and the second needle 7 is located at the most distal position.

It is preferable that the fixing member 21 includes a first insertion passage 22 extending in the direction from the distal end to the proximal end of the device, and the first needle 6 and/or the second needle 7 are/is inserted into the first insertion passage 22. The first insertion passage 22 is provided so as to penetrate the fixing member 21 in the direction from the distal end to the proximal end of the device. By providing the first insertion passage 22 in the fixing member 21 in this manner, a periphery of a point where the membranal tissue is punctured with the first needle 6 or the second needle 7 may be fixed by the fixing member 21, and the puncture with the first needle 6 or the second needle 7 becomes easy. The trajectories of the first needle 6 and the second needle 7 moving in the direction from the distal end to the proximal end of the device are stabilized.

It is preferable that the fixing member 21 includes a second insertion passage 23 extending in the direction different from the distal end to the proximal end of the device, and the first holding portion 10 or the second holding portion 11 is inserted into the second insertion passage 23. The second insertion passage 23 is preferably connected to the middle of the first insertion passage 22. In the suturing device illustrated in FIGS. 9 and 10, the first holding portion 10 is inserted into the second insertion passage 23. Meanwhile, in a case where the second holding portion 11 is inserted into the second insertion passage 23, it is preferable that the suturing device may clamp the membranal tissue when the fixing member 21 is proximally moved. By providing the second insertion passage 23 in the fixing member 21, the first holding portion 10 or the second holding portion 11 may be moved more correctly in a direction different from the distal direction and the proximal direction. It is possible to configure such that the first thread control member 8 or the second thread control member 9 distally and proximally moves by distally and proximally moving the fixing member 21. The second insertion passage 23 is preferably formed so as to extend in a direction perpendicular to the direction from the distal end to the proximal end of the device.

FIG. 11 illustrates a configuration example of the suturing device provided with the spacer described above in the suturing device illustrated in FIGS. 9 and 10. In the suturing device illustrated in FIG. 11, the second supporting portion 13 of the second thread control member 9 includes the second tubular portion 14, and the first supporting portion 12 of the first thread control member 8 is slidably disposed in the second tubular portion 14. In this case, since the first supporting portion 12 is inserted into the second tubular portion 14, both the first thread control member 8 and the second thread control member 9 may be simultaneously moved in the upward direction by moving the spacer 20 to a position under the second tubular portion 14. Both the first thread control member 8 and the second thread control member 9 may be simultaneously moved in the downward direction by proximally moving the spacer 20 from the state in FIG. 11.

This application claims the benefit of the priority date of Japanese patent application No. 2018-186971 filed on Oct. 1, 2018. All of the contents of the Japanese patent application No. 2018-186971 filed on Oct. 1, 2018 are incorporated by reference herein.

REFERENCE SIGNS LIST

1: Bi-directional medical suturing device
2: Treatment portion
3: Tubular body
4: Cutout 5: Handle
6: First needle
7: Second needle
8: First thread control member
9: Second thread control member
10: First holding portion
11: Second holding portion
12: First supporting portion
13: Second supporting portion
14: Second tubular portion
15: Connector
16: Passage
20: Spacer
21: Membranal tissue fixing member
22: First insertion passage
23: Second insertion passage
24: Membranal tissue

The invention claimed is:

1. A bi-directional medical suturing device having a proximal end and a distal end, the device comprising:
    a first needle having a tip directed toward a distal side, the first needle being movable in a longitudinal direction extending from the proximal end to the distal end;
    a second needle being disposed more distal than the first needle, the second needle having a tip directed toward a proximal side, the second needle being movable in the longitudinal direction;
    a first thread control member including a first holding portion being movable in a direction different from the longitudinal direction between a position where the first holding portion prevents a movement of the first needle and a position where the first holding portion does not prevent the movement of the first needle; and
    a second thread control member including a second holding portion being movable in a direction different from the longitudinal direction between a position where the second holding portion prevents a movement of the second needle and a position where the second holding portion does not prevent the movement of the second needle,
    the first thread control member and the second thread control member being arranged such that the first holding portion is located more distal than the first needle and more proximal than the second needle, and the second holding portion is located more distal than the first holding portion and more proximal than the second needle in a state where the first needle is located at the most proximal position and the second needle is located at the most distal position.

2. The bi-directional medical suturing device according to claim 1, wherein
    the first thread control member and the second thread control member are arranged such that the first holding portion is movable between the position where the first holding portion prevents a movement of the first needle and the position where the first holding portion does not prevent the movement of the first needle, and is movable between the position where the second holding portion prevents a movement of the second needle and the position where the second holding portion does not prevent the movement of the second needle, and/or the second holding portion is movable between the position where the second holding portion prevents a movement of the second needle and the position where the second holding portion does not prevent the movement of the second needle, and is movable between the position where the first holding portion prevents a movement of the first needle and the position where the first holding portion does not prevent the movement of the first needle.

3. The bi-directional medical suturing device according to claim 1, wherein
    the first holding portion is movable in a direction perpendicular to the longitudinal direction, and/or
    the second holding portion is movable in a direction perpendicular to the longitudinal direction.

4. The bi-directional medical suturing device according to claim 3, wherein
    the first holding portion has a rod shape extending in the direction perpendicular to the longitudinal direction, and is movable in the direction perpendicular to the direction longitudinal, and/or
    the second holding portion has a rod shape extending in the direction perpendicular to the longitudinal direction, and is movable in the direction perpendicular to the longitudinal direction.

5. The bi-directional medical suturing device according to claim 3, wherein
    the first holding portion and the second holding portion are movable in the direction perpendicular to the longitudinal direction.

6. The bi-directional medical suturing device according to claim 1, wherein
    the first needle and the second needle are overlapped with each other in cross-section as seen from the distal side or the proximal side.

7. The bi-directional medical suturing device according to claim 1, further comprising a body tissue fixing member movable in the longitudinal direction, wherein
    the fixing member includes a first insertion passage extending in the longitudinal direction, in which the first needle and/or the second needle are insertable.

8. The bi-directional medical suturing device according to claim 1, wherein
    the first thread control member includes a first supporting portion extending in the longitudinal direction, the first supporting portion being disposed more proximal than the first holding portion, and/or
    the second thread control member includes a second supporting portion extending in the longitudinal direction, the second supporting portion being disposed more proximal than the second holding portion.

9. The bi-directional medical suturing device according to claim 8, wherein
    the first thread control member and/or the second thread control member is movable in the longitudinal direction.

10. The bi-directional medical suturing device according to claim 8, wherein
    the first supporting portion includes a first tubular portion, which at least partially has a tubular shape extending in the longitudinal direction, and the second supporting portion of the second thread control member is slidably disposed in the first tubular portion, or
    the second supporting portion includes a second tubular portion, which at least partially has a tubular shape extending in the longitudinal direction, and the first supporting portion of the first thread control member is slidably disposed in the second tubular portion.

11. The bi-directional medical suturing device according to claim 9, further comprising a body tissue fixing member movable in the longitudinal direction, wherein
    the fixing member includes a second insertion passage extending in a direction different from the longitudinal direction, and the first holding portion or the second holding portion is insertable into the second insertion passage, and the first thread control member or the second thread control member are movable in the longitudinal direction by moving the fixing member in the longitudinal direction.

12. The bi-directional medical suturing device according to claim 8, wherein the first holding portion and the first supporting portion of the first thread control member are movable in a direction perpendicular to the longitudinal direction, and the second holding portion and the second supporting portion of the second thread control member are movable in a direction perpendicular to the longitudinal direction.

13. The bi-directional medical suturing device according to claim 12, wherein, when the direction perpendicular to the longitudinal direction is set to a vertical direction, a direction in which the first holding portion moves from the position where the first holding portion prevents a movement of the first needle to the position where the first holding portion does not prevent the movement of the first needle is set to a downward direction, and a direction opposite to the downward direction is set to an upward direction, the bi-directional medical suturing device further comprises a spacer being movable in the longitudinal direction, the spacer being disposed under the first supporting portion and/or the second supporting portion, such that i) by moving the spacer distally, the first holding portion and the first supporting portion move in the upward direction, and/or the second holding portion and the second supporting portion move in the upward direction, and ii) by moving the spacer proximally, the first holding portion and the first supporting portion move in the downward direction, and/or the second holding portion and the second supporting portion move in the downward direction.

14. A bi-directional medical suturing device comprising:
a tubular body having a proximal end and a distal end and extending in a longitudinal direction from the proximal end to the distal end;
a first needle having a tip directed toward a distal side, the first needle disposed in the tubular body so that the first needle is movable in the longitudinal direction;
a second needle having a tip directed toward a proximal side, the second needle disposed in the tubular body so that the second needle is movable in the longitudinal direction and located at a more distal position than the first needle;
a first thread control member including a first holding portion being movable in a direction different from the longitudinal direction between a position where the first holding portion prevents a movement of the first needle and a position where the first holding portion does not prevent the movement of the first needle; and
a second thread control member including a second holding portion being movable in a direction different from the longitudinal direction between a position where the second holding portion prevents a movement of the second needle and a position where the second holding portion does not prevent the movement of the second needle,
the first thread control member and the second thread control member being arranged such that the first holding portion is located more distal than the first needle and more proximal than the second needle, and the second holding portion is located more distal than the first holding portion and more proximal than the second needle in a state where the first needle is located at the most proximal position and the second needle is located at the most distal position.

\* \* \* \* \*